United States Patent [19]

Hermann

[11] Patent Number: 5,702,417
[45] Date of Patent: Dec. 30, 1997

[54] BALLOON LOADED DISSECTING INSTRUMENTS

[75] Inventor: George D. Hermann, Los Gates, Calif.

[73] Assignee: General Surgical Innovations, Inc., Cupertino, Calif.

[21] Appl. No.: 447,124

[22] Filed: May 22, 1995

[51] Int. Cl.$^6$ .................................................. A61M 29/00
[52] U.S. Cl. .................................................. 606/194; 604/96
[58] Field of Search .................................................. 606/194, 154; 604/96

[56] References Cited

U.S. PATENT DOCUMENTS

| | | | |
|---|---|---|---|
| 4,312,353 | 1/1982 | Shahbabian | 606/192 |
| 4,493,711 | 1/1985 | Chin et al. | 604/271 |
| 4,779,611 | 10/1988 | Grooters et al. | 128/4 |
| 4,932,959 | 6/1990 | Hovzewski et al. | 606/194 |
| 5,032,113 | 7/1991 | Burns | 604/96 |
| 5,183,463 | 2/1993 | Debbas | 604/98 |
| 5,188,630 | 2/1993 | Christoudias | 606/1 |
| 5,197,971 | 3/1993 | Bonutti | 606/192 |
| 5,269,753 | 12/1993 | Wilk | 604/49 |
| 5,307,814 | 5/1994 | Kressel et al. | 128/653 |
| 5,331,975 | 7/1994 | Bonutti | 128/898 |
| 5,346,504 | 9/1994 | Ortiz et al. | 606/192 |
| 5,359,995 | 11/1994 | Sewell, Jr. | 128/20 |
| 5,373,840 | 12/1994 | Knighton | 128/4 |
| 5,383,889 | 1/1995 | Warner et al. | 606/192 |
| 5,391,178 | 2/1995 | Yapor | 606/192 |
| 5,425,357 | 6/1995 | Moll et al. | 128/20 |
| 5,454,365 | 10/1995 | Bonutti | 600/204 |
| 5,496,345 | 3/1996 | Kieturakis et al. | 606/192 |
| 5,514,153 | 5/1996 | Bonutti | 606/190 |

FOREIGN PATENT DOCUMENTS 0411767  8/1991  France ........................ A61B 19/00

OTHER PUBLICATIONS

U.S. application No. 08/267,484, Fogarty et al., filed 1882.

*Primary Examiner*—Michael Buiz
*Assistant Examiner*—Kevin Truong
*Attorney, Agent, or Firm*—Lyon & Lyon LLP

[57] ABSTRACT

Balloon loaded dissection devices with elongate balloon and a pushing member are disclosed for creating a tunnel alongside an elongate vessel in the body. The devices may utilize an elongate balloon of any suitable length which may be formed of an elastic or non-elastic material. The balloon may be of double walled construction and may be provided with a central lumen which may receive a guide rod, scope or other surgical instrument. The device may have a support tube secured to the inner wall of the balloon to provide columnar support for the apparatus. The support tube receives the guide rod, scope or other surgical instrument and may have a stop member to translate pushing force applied to the guide rod or scope to pushing force on the apparatus. By using the guide rod or scope as a pushing member the apparatus may be advanced alongside the vessel it is desired to dissect free from attached tissue. A balloon cover which may be elastic or resilient is provided to surround the balloon and facilitate compression of the balloon after it is deflated.

5 Claims, 4 Drawing Sheets

BALLOON LOADED DISSECTING INSTRUMENTS

FIELD OF THE INVENTION

This invention relates to methods and devices for endoscopic vascular surgery, in particular to methods and devices for dissecting tissue to create a working space over a blood vessel.

BACKGROUND OF THE INVENTION

Numerous surgical procedures have been developed to replace arteries that have become blocked by disease. The aortocoronary bypass surgery is perhaps the most important of these bypass operations. The coronary arteries supply blood to the heart. As a result of aging and disease, coronary arteries may become blocked by plaque deposits, stenosis, or cholesterol. In some instances, these blockages can be treated with atherectomy, angioplasty or stent placement, and coronary bypass surgery is not required. Coronary bypass surgery is required when these other methods of treatment cannot be used or have failed to clear the blocked artery. In coronary bypass surgery, a vein is harvested from elsewhere in the body and grafted into place between the aorta and the coronary artery below the point of blockage. An illustration of this surgery is shown in FIG. 1, which shows the heart 1 and the right anterior coronary artery 2 and the left anterior coronary artery 3 which supply blood to the heart. The right anterior coronary artery 2 is blocked in its proximal segment at 2a, as shown. This blockage has been bypassed by grafting a segment of vein 4 between the aorta 5 and the distal segment 2b of the right anterior coronary artery 2. Similarly, the left anterior coronary artery 3 may be blocked, and may require bypass with a length of vein 4a between the aorta and the distal segment 3b of the left anterior artery. The operation requires access to the heart, which means that the chest cavity must be opened completely.

The coronary bypass surgery requires a length of vein or artery for the graft. It is preferred to use a vein taken from the patient undergoing the bypass surgery. The patient is a ready source of suitable veins that will not be rejected by the body after transplantation and grafting onto the aorta and coronary artery. The saphenous vein in the leg is the best substitute for small arteries such as the coronary arteries, and it is the preferred vein for use in coronary bypass surgery. This is because the saphenous vein is typically 3 to 5 mm in diameter, about the same size as the coronary arteries. Also, the venous system of the legs is sufficiently redundant so that after removal of the saphenous vein other veins that remain in the leg are adequate to provide adequate return blood flow. The cephalic vein in the arm is an alternative that is sometimes used.

A typical operation previously required to harvest the saphenous vein is illustrated in FIG. 2. The surgeon cuts into the leg to allow access to the saphenous vein and cuts the vein from the leg. To expose the saphenous vein 6, the surgeon makes a series of incisions from the groin 7 to the knee 8 or the ankle 9, leaving a one or more skin bridges 10 along the line of the incisions. Some surgeons make one continuous incision from the groin to the knee or ankle. Handling of the vein must be kept to a minimum, but the vein must be removed from connective tissue that requires some force to remove. After exposing the vein, the surgeon grasps it with his fingers while stripping off the surrounding tissues with dissecting scissors or other scraping instruments. The surgeon uses his fingers and blunt dissection tools to pull and lift (or mobilize) the vein from the surrounding tissue. The vein is mobilized or pulled as far as possible through each incision. To reach under the skin bridges, the surgeon lifts the skin with retractors and digs the vein free. While stripping the vein, the surgeon will encounter the various tributary veins that feed into the saphenous vein. These tributaries must be ligated and divided. To divide and ligate tributaries that lie under the skin bridges, the surgeon may need to cut one end of the saphenous vein and pull it under the skin bridge to gently pull the vein out from under the skin bridge until the tributary is sufficiently exposed so that it may be ligated and divided. When the vein has been completely mobilized, the surgeon cuts the proximal and distal ends of the vein and removes the vein from the leg. After removal, the vein is prepared for implantation into the graft site, and the long incisions made in the leg are stitched closed.

The procedure described above can be used to harvest veins for a femoral popliteal bypass, in which an occluded femoral artery is bypassed from above the occlusion to the popliteal artery near the level of the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery.

As can be seen from the description of the harvesting operation, the harvesting operation is very traumatic in its own right. In the case of coronary artery bypass, this operation is carried out immediately before the open chest operation required to graft the harvested vein into the coronary arteries. The vein harvesting operation is often the most troublesome part of the operation. The long incisions created in the leg can be slow to heal and very painful. Complications resulting from the vein harvesting operation can also hinder the patient's recovery from the entire operation.

The method of vein harvesting presented herein is accomplished with laparoscopic procedures. This allows the veins to be harvested in an operation that requires only a few small incisions. Endoscopic surgical techniques for operations such as gall bladder removal and hernia repair are now common. The surgeon performing the operation makes a few small incisions and inserts long tools, including forceps, scissors, and staplers, into the incision and deep into the body. Viewing the tools through a laparoscope or a video display from the laparoscope, the surgeon can perform a wide variety or maneuvers, including cutting and suturing operations, necessary for a wide variety of surgical procedures and operations.

Minimally invasive procedures for vein removal have been proposed. Knighton, Endoscope and Method for Vein Removal, U.S. Pat. No. 5,373,840 shows a method of cutting the saphenous vein at one end, and grasping the vein with graspers or forceps, then sliding a ring over the vein while holding it. Knighton uses a dissecting tool with an annular cutting ring, and requires that the saphenous vein be overrun or progressively surrounded with the dissecting tool and the endoscope, so that after the endoscope has been inserted as far as it will go, the entire dissected portion of the vein has been pulled into the lumen of the endoscope. As shown in FIGS. 1 and 10 of Knighton, the method requires deployment of forceps inside the annular dissection loop, and it requires deployment of the loop and graspers inside the endoscope lumen. The blood vessel must be cut and grasped by the forceps before it can be dissected by the dissecting ring.

The method of vein harvesting disclosed herein uses a balloon to assist in dissecting the harvested vein. An uninflated tubular balloon wrapped around a guide rod or endoscope and covered with an easily removable balloon cover is inserted into one of the small incisions and pushed along the vein to create a small tunnel over the vein. When the balloon is in place over the vein, the balloon cover may be left in place or it may be removed and the balloon is inflated to enlarge the tunnel and create a work space for insertion of endoscopic instruments. The guide rod or endoscope may be removed to allow other endoscopic instruments to be passed into the tunnel through the balloon.

SUMMARY OF THE INVENTION

The methods and devices disclosed herein allow surgeons to harvest veins without making long incisions as has previously been required.

In a preferred embodiment, a blunt loaded balloon dissector has an elongate balloon of any suitable length which may be formed of an elastic or non-elastic material. The balloon may be of double walled construction and may be provided with a central lumen which may receive a guide rod, scope or other surgical instrument. The device may have a support tube secured to the inner wall of the balloon to provide columnar support for the apparatus. The support tube receives the guide rod, scope or other surgical instrument and may have a stop member to translate pushing force applied to the guide rod or scope to pushing force on the apparatus. By using the guide rod or scope as a pushing member the apparatus may be advanced alongside the vessel it is desired to dissect free from attached tissue. A balloon cover which may be elastic or resilient is provided to surround the balloon and facilitate compression of the balloon after it is deflated.

In another embodiment of the invention, another pushable balloon dissection device is provided which also may utilize an elongate balloon. The balloon in this embodiment is elongate and may have a central lumen to receive a scope or other laparoscopic instrument. The apparatus has a guide tube which receives a guide rod with a slender metal rod and enlarged tip. The guide rod is utilized as a pushing member. A balloon cover may also be provided in this embodiment.

The present devices permit minimally invasive procedures which require just two small incisions, one at either end of the saphenous vein, to be performed. The procedure is accomplished with laparoscopic instruments under the guidance of a laparoscope. The surgeon makes one small incision at each end of the saphenous vein. After making the incisions, the surgeon inserts a tunneling instrument or blunt dissector which carries a long balloon into one incision and advances or pushes along the saphenous vein to make a small tunnel along the saphenous vein. The surgeon then inflates the long balloon to enlarge the tunnel. When the tunnel is enlarged to an appropriate size, the surgeon removes the balloon and seals the tunnel at both ends. The surgeon then injects carbon dioxide into the tunnel at sufficient pressure (typically 5–15 mm Hg) to inflate the tunnel and create room for laparoscopic instruments. The surgeon then inserts a laparoscope through the seal to provide a view of the procedure, and inserts a laparoscopic vein harvesting device described in co-pending U.S. application Ser. No. 08/444,424 entitled, "Methods and Devices for Blood Vessel Harvesting," the disclosure of which is hereby incorporated by reference in its entirety, to dissect the connective tissue from the vein, identify side branches, and remove the vein from the leg. After the vein is loosened or dissected free from its channel in the leg, the surgeon can cut the proximal and distal ends of the vein and easily pull the vein from the leg. The small skin incisions are stitched so that they may heal. The small incisions heal much more readily, with fewer complications and far less pain, than the open procedures now in use.

DETAILED DESCRIPTION OF DRAWINGS

DETAILED DESCRIPTION OF A PREFERRED EMBODIMENT

Figure 4:
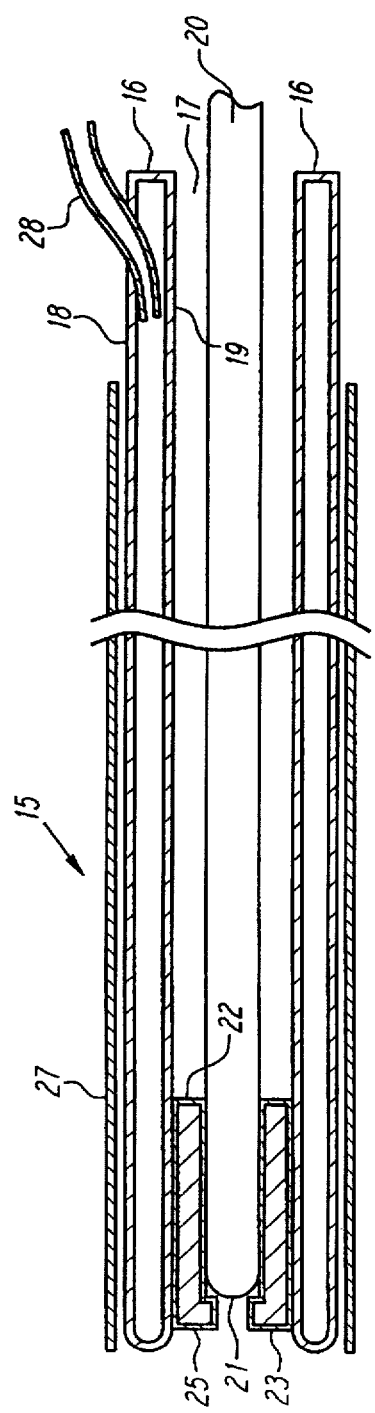
FIG. 4 shows a balloon dissector according to the invention uninflated and ready for insertion.

FIG. 4 shows an embodiment of a balloon loaded blunt dissector 15 in its uninflated state with a balloon 16 packed inside the device. The balloon 16 is a nonelastic balloon or bladder and is cylindrical or tubular with a central lumen 17. The balloon 16 has two walls 18 and 19 and may be described as a double walled balloon tube. The balloon 16 may be made of polyethylene, polyurethane, polyamide and other nonelastic materials as well as latex and other elastic materials. The balloon 16 may be any suitable length, for example 12 to 24 inches long, to provide a tunnel of convenient length when harvesting the saphenous vein. The balloon 16 may be any convenient diameter or width, for example 2 to 3 inches, to allow laparoscopic instruments to fit and operate conveniently within the tunnel created by the balloon 16. The balloon tube 16 may have any suitable cross-sectional shape.

Figure 5:
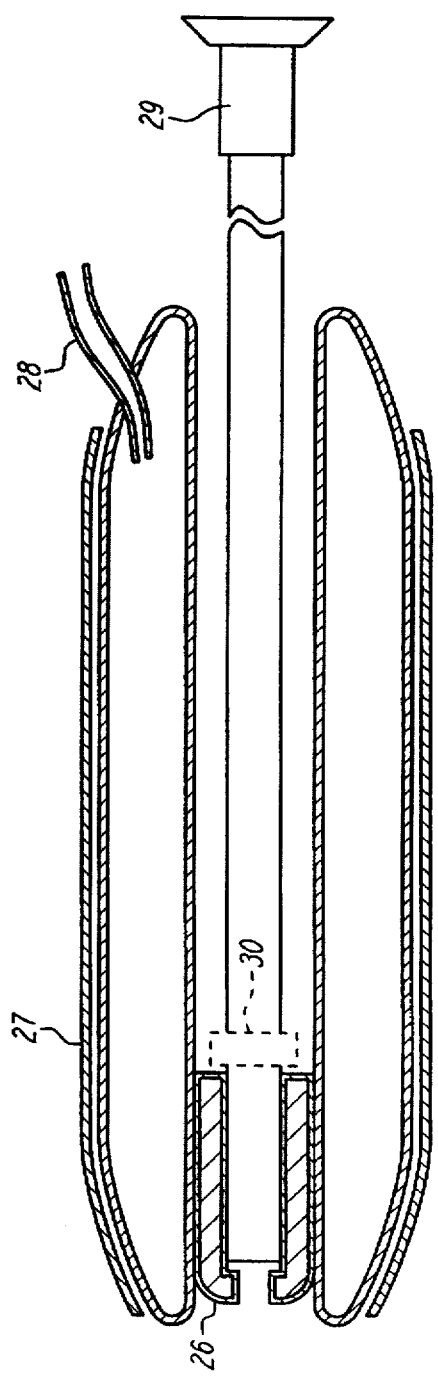
FIG. 5 shows a balloon dissector according to the invention in its inflated state.

A guide rod 20 with a blunt or rounded tip 21 is disposed in the central lumen 17 of the double walled balloon tube 16. The guide rod 20 is used as a pushing member to push the balloon 16 through body tissue. A support tube 22 may be provided to give some columnar support to the device and provide a stop member or coupling member to translate pushing force applied to the guide rod 20 to pushing action on the balloon tube 16. The support tube 22 may have an overhanging lip 23 which obstructs passage of the guide rod 20 or endoscope 29 (if provided). Alternatively, the guide rod 20 or endoscope 29 can be fitted with a stop collar 30 to engage the support tube 22 (as shown in FIG. 5). The support tube 22 may have a square tip 25 as in FIG. 4 or a rounded tip 26 as shown in FIG. 5. The guide rod 20 and support tube 22 are used to push the balloon 16 along the saphenous vein or other desired pathway between tissue layers. Use of the support tube 22 permits the guide rod 20 or endoscope 29, if utilized as the pushing member, to be removably received by the apparatus 15. This allows the apparatus 15 to use fairly expensive and nondisposable devices such as the endoscope as the pushing member. If visualization is not needed or desired, the balloon 16 may be sealed to a disposable pushing member and may be coupled to the pushing member with adhesives, heat sealing or integral construction or any other coupling means.

A balloon cover 27 surrounds the balloon tube 16 and provides a protective sheath during placement of the balloon loaded dissector 15. The balloon cover 27 may be a thin sheath of polyethylene or other plastic film, or it may be a more rigid tube of PVC, PTFE, PETG, polyethylene or other plastic. The balloon cover 27 may be elastic or resilient so that it serves to compress the balloon 16, so that the balloon 16 quickly and automatically collapses upon deflation. The balloon cover 16 may be made resilient by choosing a resilient material such as a thin sheet of polyethylene which is sufficiently resilient and elastic under the pressure used to inflate the balloon 16. The balloon 16 itself may also be made of polyethylene, and may be a thick polyethylene which is nonelastomeric under range of pressure used to inflate the balloon 16. When the balloon 16 and balloon cover 27 are made of the same material or a miscible material, the balloon 16 may be heat sealed to the balloon cover 27 at various points to prevent the balloon cover 27 from inadvertently slipping off the balloon 16. When the balloon 16 and balloon cover 27 are made of different or immiscible materials, they may be attached with adhesive or through the use of other suitable fasteners.

Figure 1:
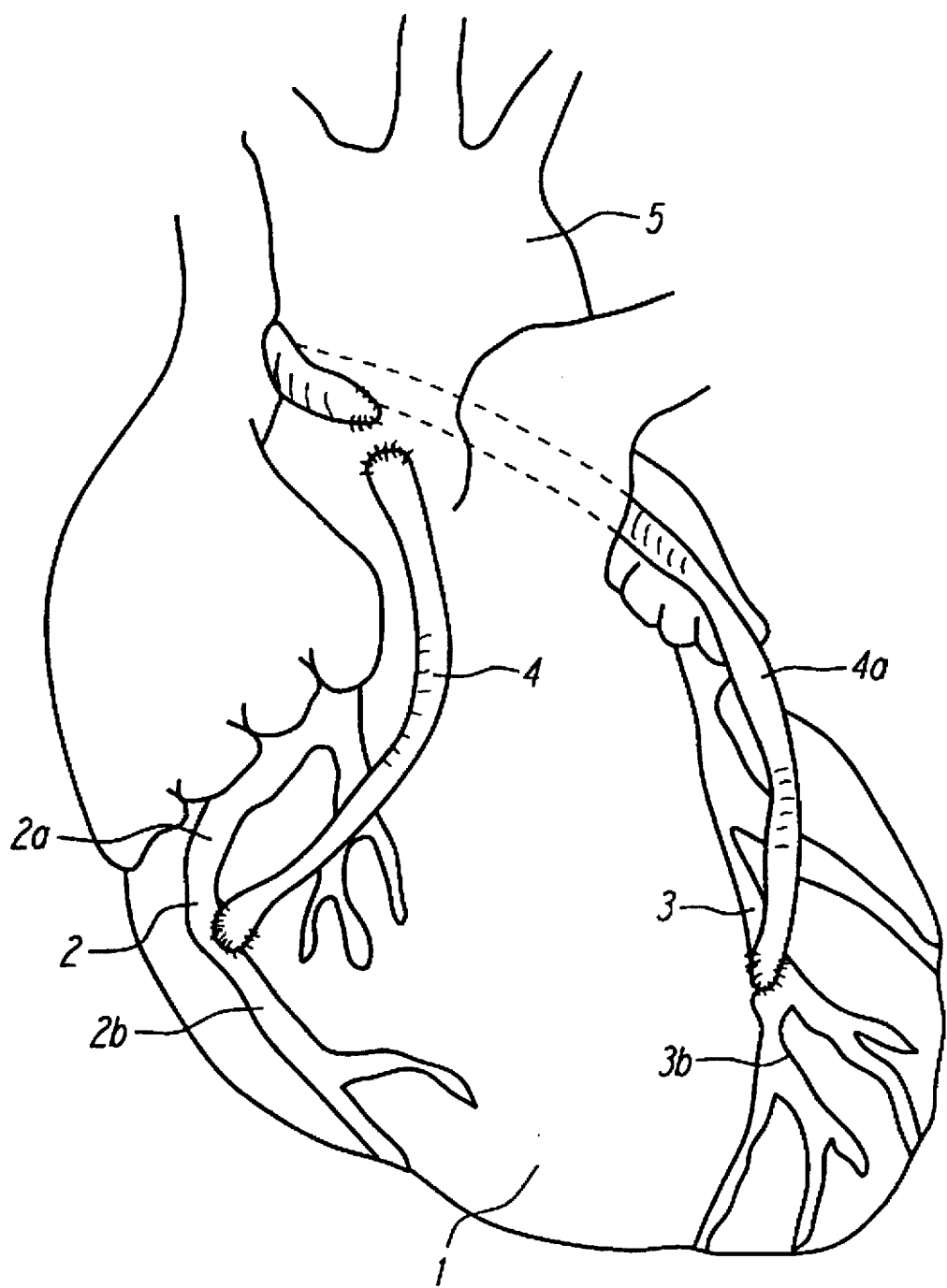
FIG. 1 is a front view of the heart showing a vein grafted from the aorta to the right anterior coronary artery, bypassing the proximal segment of the right anterior coronary artery.
Figure 2:
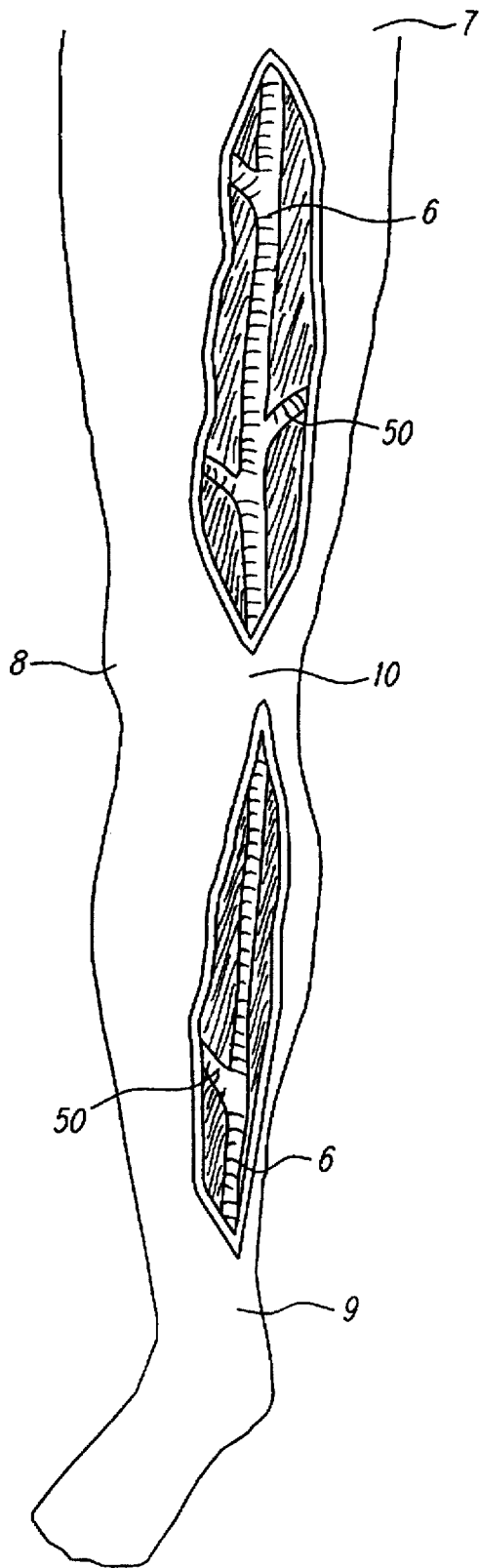
FIG. 2 is a view of the leg showing the incisions necessary for harvesting the saphenous vein using a traditional open procedure.
Figure 3:
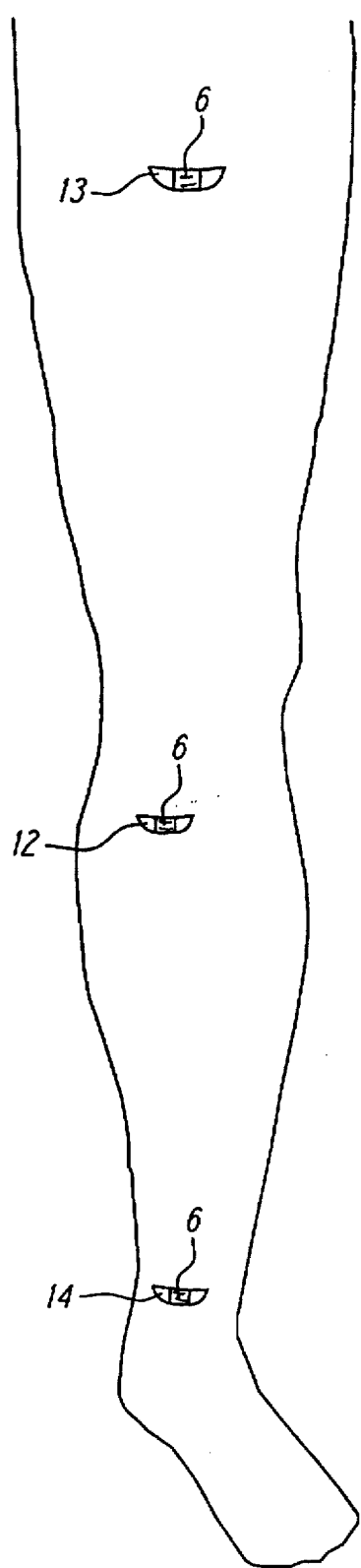
FIGS. 3, 3a and 3b are views of the leg showing the incisions necessary for harvesting the saphenous vein using the methods presented herein.

In the preferred embodiment of a method of using the devices disclosed herein, the surgeon uses a balloon loaded dissector to create a working space under the skin and over the saphenous vein suitable for laparoscopic techniques. The surgeon makes one or more incisions as shown in FIG. 3, to expose the saphenous vein. These incisions are referred to as cut-downs. An incision at the knee 12, an incision at the groin 13, or an incision close to the ankle 14 can be used. In FIG. 3, the saphenous vein 6 can be seen through the cut-downs 12, 13, and 14. It will be apparent from the description that the use of three or four incisions to harvest the entire saphenous vein is merely a matter of convenience, and those particularly skilled in laparoscopic procedures may require fewer incisions, and smaller incisions than illustrated may be required.

After insertion, the balloon loaded blunt dissector 15 is pushed along the blood vessel until the balloon tube 16 is located over the desired length of the saphenous vein. When the balloon 16 is properly in place it occupies a narrow tunnel over the saphenous vein. When in place, the balloon 16 is inflated through inflation tube 28. As shown in FIG. 5, the outer walls expand under inflation and the balloon cover 27 stretches as the balloon 16 is inflated. The expansion of the balloon 16 enlarges the tunnel. The outer diameter of the balloon tube 16 defines the size of the tunnel that is created, and the outer diameter may be controlled during manufacture and during inflation. Also as shown in FIG. 5, the guide rod 20 may be conveniently replaced with an endoscope 29 which can also serve as the pushing member. The endoscope 29 can be chosen to have an outer diameter matching the support tube, or it can be provided with a stop collar 30, both constructions serving to couple the endoscope 29 to the balloon tube 16 so that pushing on the endoscope 29 serves to push the balloon 16 into the body.

When the balloon 16 is deflated through the inflation tube 28, the balloon cover 27 serves to compress and collapse the balloon 16 and squeeze the inflation fluid out of the balloon 16, thus returning the balloon 16 to the collapsed state shown in FIG. 4. After the balloon 16 has been collapsed by the elastic force of the balloon cover 27, the device 15 may be further advanced or pulled-back from its position in the body, and repositioned at another area of interest. When the balloon 16 is repositioned, it may be re-inflated to enlarge the tunnel. The balloon may be repeatedly inflated and deflated in this manner. Alternatively, the balloon cover 27 may be removed by pulling it proximally out of the incision to allow the balloon 16 to expand.

Figure 6:
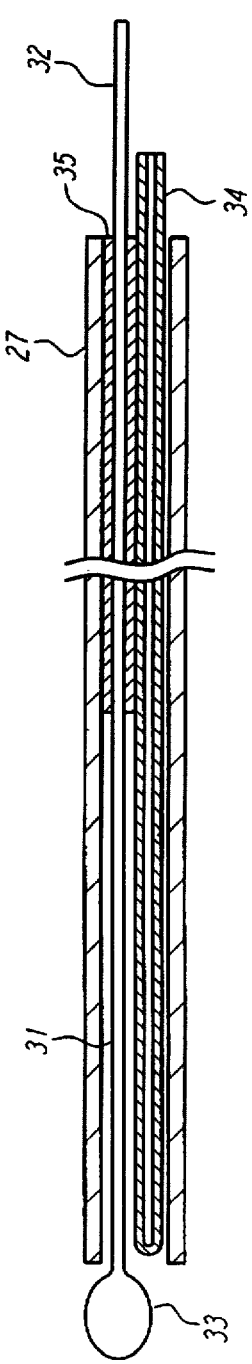
FIG. 6 is a cross-section of an alternate embodiment of a balloon dissector in its uninflated state.

FIG. 6 shows an alternate embodiment of a balloon loaded blunt dissector. The guide rod 31 is provided with a slender metal rod 32 fitted with an enlarged tip or olive tip 33. The guide rod 31 may be replaced by a scope if visualization is desked. The balloon 34 is a long slender cylindrical balloon, with or without a central lumen. A guide tube 35 is attached to the outside of the balloon 34 and the guide rod 31 fits through the guide tube 35. The balloon 34 is uninflated in FIG. 6, and the balloon 34 and guide tube 35 are shown inside the balloon cover 27. The balloon 34 of FIG. 6 is used in the same way as the balloon 16 of FIGS. 4 and 5.

Figures 3A, 3B:
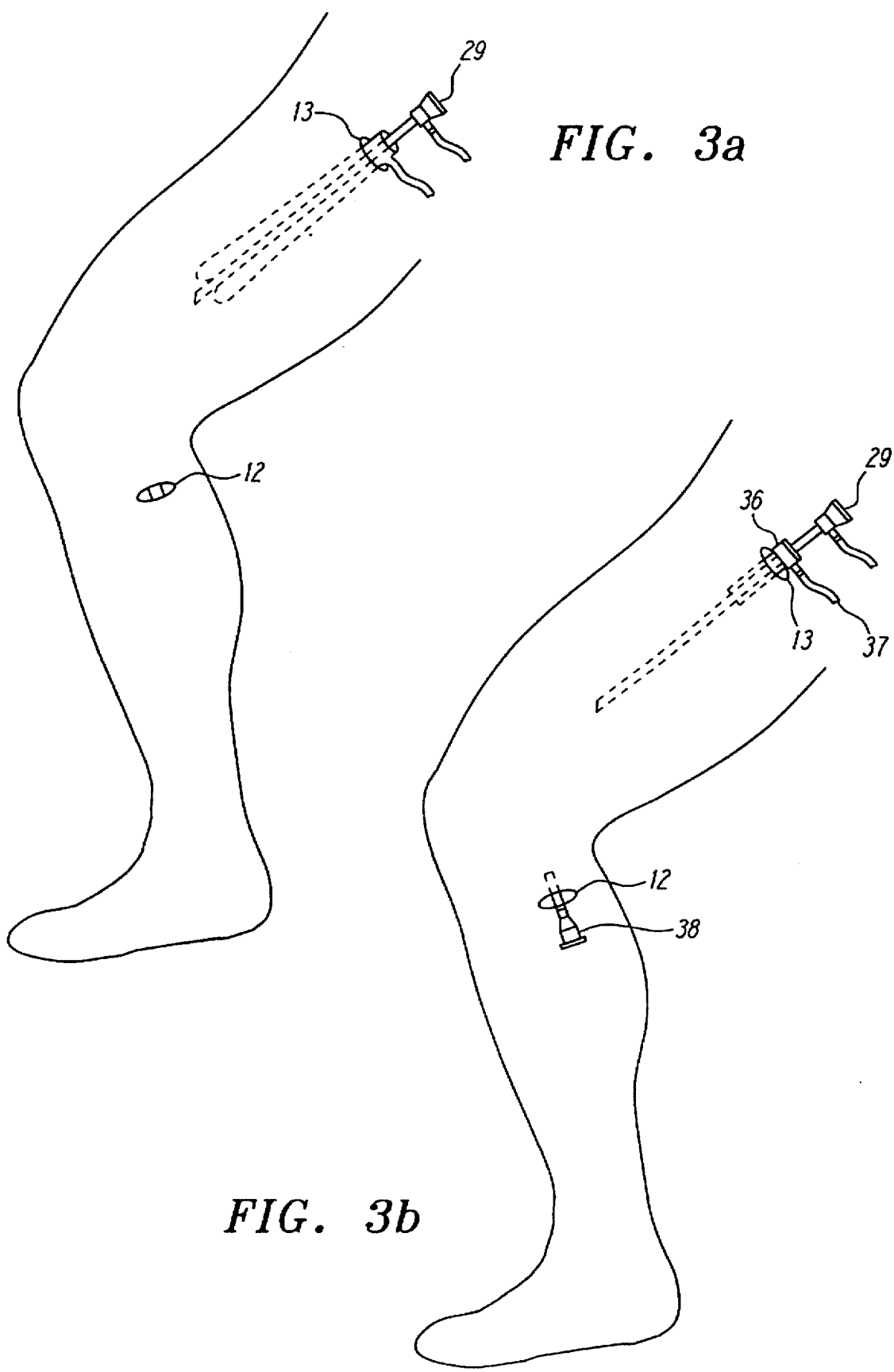

In operation, the apparatus is slipped over an endoscope (if utilized) or guide rod 31 and the balloon cover 27 is slipped over the apparatus. It is expected that use of an endoscope will be preferred because it allows for visualization of the anatomy at its distal tip as the apparatus pushes through the fat layer overlying the saphenous vein. The apparatus is inserted either directly into the incision or is introduced through a cannula. After the guide rod 31 and balloon 34 are in place over the blood vessel, the balloon cover 27 can be pulled out of the incision, and may be provided with a weakened section to facilitate removal. The balloon cover 27 may be pulled back gradually as the balloon 34 is inserted to uncover that portion of the balloon 34 which is inside the body, and the balloon 34 can be inflated to dissect a larger tunnel in the early stages of insertion. The balloon cover 27 may also be left in place and, if made of a resilient material, can be used to compress the balloon 34 after deflation to facilitate repositioning of the assembly. After full insertion, in a preferred method of use, the balloon 34 may be left in place in the tunnel while the endoscope is utilized to view the interior surfaces of the body at the tip of the apparatus, as shown in FIG. 3a. If the balloon 34 is provided with a central lumen, endoscopic instruments may be passed through said central lumen to perform surgical procedures on body parts such as the saphenous vein and communicating veins of the leg. In situations where it is desirable to insufflate the tunnel created by the balloon 34, the balloon 34 may be deflated and pulled out of the tunnel through cut-down 13, and a cannula port 36 with insufflation tube 37 may be inserted into the same cut-down as shown in FIG. 3b. A secondary endoscopic access port 38 may be inserted into the knee incision 12 to pass a variety of instruments into the work space.

The step of removing the balloon cover 27 may be avoided if the balloon cover 27 is perforated along a number of longitudinal lines and sealed to the balloon 34 along interstitial longitudinal lines, so that expansion of the balloon 34 tears the balloon cover 27 to allow expansion, but the pieces stay fixed to the balloon 34 so that they may be removed easily.

The balloon dissectors disclosed herein can be used in other procedures besides dissection for vein harvesting, and its description in that environment is merely intended to be illustrative of the device. It is readily apparent that the devices and methods may be used for tunneling and enlarging working spaces over other long organs of the body. Various arteries and veins must be exposed and mobilized for other operations, such as popliteal bypass, or a dialysis vein loop. In these operations, a vein must be harvested, and the sites at which the vein will be attached or anastomosed must also be uncovered. The balloon dissector may also be used to gain access to any blood vessel for any type of vascular surgery. For example, communicating veins or perforators in the calf may be exposed by dissecting the muscles deep within the calf to expose these blood vessels to accomplish a Linton procedure laparoscopically. The devices and methods may be used to expose those portions of the arteries to which grafts will be placed.

Other vessels may be dissected from surrounding tissue, such as fallopian tubes, spermatic cords, bile ducts, intestines and others. These vessels may be dissected and mobilized laparoscopically using the techniques described above. The device may also be used to retrofit any scope with a balloon dissector to dissect along a tunnel under direct vision. The balloon can be used to guide or support any scope within an existing space that needs periodic dilation to permit advancement of the scope. For example, a colonoscope may be fitted with the balloon dissector and used to facilitate insertion of the colonoscope into the colon, especially around the splenic flexure, by inflating the balloon when the tip of the colonoscope approaches the splenic flexure. A urethral scope may be fitted with the balloon dissector to facilitate insertion of the scope into the urethra, which often requires dilation before insertion of a scope. The balloon dissector may be used in combination with any scope as an anchor, which while inflated serves to hold a scope in place within the body. While the preferred embodiments of the devices and methods have been described, they are merely illustrative of the principles of the invention. Other embodiments and configurations may be devised without departing from the spirit of the inventions and the scope of the appended claims.

I claim:

1. A method of dissecting layers of tissue to create a working space between the tissue layers, said method comprising:

providing an elongate balloon tube and a substantially rigid pushing member disposed within the balloon tube, the pushing member being coupled to the balloon tube;

inserting the balloon tube between the layers of tissue;

pushing the balloon tube by pushing the pushing member along a path to be dissected between the layers of tissues; and inflating the balloon tube before the balloon tube is inserted between the tissue layers to cause the balloon tube to expand and create the working space between the layers of tissue.

2. A method of dissecting layers of tissue to create a working space between the tissue layers, said method comprising:

providing an elongate balloon tube and a substantially rigid pushing member disposed within the balloon tube, the pushing member being coupled to the balloon tube;

providing a balloon cover surrounding the balloon tube;

inserting the balloon tube between the layers of tissue;

pushing the balloon tube by pushing the pushing member along a path to be dissected between the layers of tissue;

removing the balloon cover from the balloon tube after the balloon tube has been pushed between the tissue layers along the path to be dissected; and inflating the balloon tube to cause the balloon tube to expand and create the working space between the layers of tissue.

3. A method of dissecting layers of tissue to create a working space between the tissue layers, said method comprising:

providing an elongate balloon tube and a substantially rigid pushing member disposed within the balloon tube, the pushing member being coupled to the balloon tube;

inserting the balloon tube between the layers of tissue;

pushing the balloon tube by pushing the pushing member along a path to be dissected between the layers of tissue;

inserting an endoscope into a central lumen in the balloon tube and viewing the path between the tissue layers through the endoscope as the balloon tube is pushed between the tissue layers along the path to be dissected; and inflating the balloon tube to cause the balloon tube to expand and create the working space between the layers of tissue.

4. A method of dissecting layers of tissue to create a working space between the tissue layers, said method comprising:

providing an elongate balloon tube and a substantially rigid pushing member disposed within the balloon tube, the pushing member being coupled to the balloon tube;

inserting the balloon tube between the layers of tissue;

pushing the balloon tube by pushing the pushing member alongside the saphenous vein in the leg; and inflating the balloon tube to cause the balloon tube to expand to dissect the saphenous vein free from connective tissues.

5. A method of dissecting layers of tissue to create a working space between the tissue layers, said method comprising:

providing an elongate balloon tube and a substantially rigid pushing member disposed within the balloon tube, the pushing member being coupled to the balloon tube;

inserting the balloon tube between the layers of tissue;

pushing the balloon tube by pushing the pushing member along a path to be dissected between the layers of tissue;

inflating the balloon tube to cause the balloon tube to expand and create the working space;

deflating the balloon tube;

repositioning the balloon tube by moving the balloon tube between the tissue layers along the path to be dissected to a point remote from the point where the balloon tube was first inflated; and inflating the balloon tube again to selectively enlarge the working space between the layers of tissue.

* * * * *

UNITED STATES PATENT AND TRADEMARK OFFICE
CERTIFICATE OF CORRECTION

PATENT NO. : 5,702,417

DATED : December 30, 1997

INVENTOR(S) : George D. Hermann

It is certified that error appears in the above-identified patent and that said Letters Patent is hereby corrected as shown below:

In column 4, line 14, delete "fight" and insert therefor –right–.

In column 6, line 13, delete "desked" and insert therefor –desired–.

Signed and Sealed this

Fourth Day of August, 1998

Attest:

Attesting Officer

BRUCE LEHMAN

Commissioner of Patents and Trademarks